(12) United States Patent
Tuval et al.

(10) Patent No.: US 10,806,570 B2
(45) Date of Patent: Oct. 20, 2020

(54) PROSTHETIC HEART VALVE HAVING IDENTIFIERS FOR AIDING IN RADIOGRAPHIC POSITIONING

(71) Applicant: Medtronic, Inc., Minneapolis, MN (US)

(72) Inventors: Yossi Tuval, Netanya (IL); Raphael Benary, Tel Aviv (IL)

(73) Assignee: Medtronic, Inc., Minneapolis, MN (US)

( * ) Notice: Subject to any disclaimer, the term of this patent is extended or adjusted under 35 U.S.C. 154(b) by 183 days.

(21) Appl. No.: 15/939,497

(22) Filed: Mar. 29, 2018

(65) Prior Publication Data

US 2018/0214265 A1 Aug. 2, 2018

Related U.S. Application Data

(63) Continuation of application No. 14/641,545, filed on Mar. 9, 2015, now Pat. No. 9,943,407, which is a continuation of application No. 12/559,945, filed on Sep. 15, 2009, now Pat. No. 8,998,981.

(60) Provisional application No. 61/192,201, filed on Sep. 15, 2008.

(51) Int. Cl.
*A61F 2/24* (2006.01)
*A61B 34/20* (2016.01)
*A61B 90/00* (2016.01)

(52) U.S. Cl.
CPC ............ *A61F 2/2418* (2013.01); *A61B 34/20* (2016.02); *A61F 2/2436* (2013.01); *A61B 2090/376* (2016.02); *A61F 2220/0016* (2013.01); *A61F 2220/0075* (2013.01); *A61F 2230/005* (2013.01); *A61F 2230/008* (2013.01); *A61F 2230/0054* (2013.01); *A61F 2250/0098* (2013.01)

(58) Field of Classification Search
CPC .... A61F 2/2409; A61F 2/2418; A61F 2/2236; A61F 2250/0096–0098
See application file for complete search history.

(56) References Cited

U.S. PATENT DOCUMENTS

| | | | |
|---|---|---|---|
| 3,334,629 A | 8/1967 | Cohn | |
| 3,409,013 A | 11/1968 | Berry | |
| 3,540,431 A | 11/1970 | Mobin-Uddin | |
| 3,587,115 A | 6/1971 | Shiley | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |

(Continued)

FOREIGN PATENT DOCUMENTS

| CN | 2007-100074433 | 10/2007 |
|---|---|---|
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — William H Matthews
(74) *Attorney, Agent, or Firm* — Dicke, Billig & Czaja, PLLC

(57) ABSTRACT

A prosthetic heart valve having identifiers for aiding in radiographic positioning is described.

20 Claims, 8 Drawing Sheets

(56) References Cited

U.S. PATENT DOCUMENTS

| | | |
|---|---|---|
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 7/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,344,442 A | 9/1994 | Deac |
| 5,350,398 A | 9/1994 | Pavcnik et al. |
| 5,354,330 A | 10/1994 | Hanson et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,996 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,908,451 A | 6/1999 | Yeo |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,022,374 A | 2/2000 | Imran |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |

(56) References Cited

U.S. PATENT DOCUMENTS

| | | |
|---|---|---|
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,296,662 B1 | 10/2001 | Caffey |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,312,465 B1 | 11/2001 | Griffin et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,361,557 B1 | 3/2002 | Gittings et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,018,406 B2 | 3/2006 | Seguin et al. |
| 7,018,408 B2 | 3/2006 | Bailey et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,137,184 B2 | 11/2006 | Schreck |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,806,919 B2 | 10/2010 | Bloom et al. |
| 8,052,750 B2 | 11/2011 | Tuval et al. |
| 8,784,478 B2 | 7/2014 | Tuval et al. |
| 8,998,981 B2 | 4/2015 | Tuval et al. |
| 2001/0002445 A1 | 3/2001 | Vesely |

(56) References Cited

U.S. PATENT DOCUMENTS

| | | |
|---|---|---|
| 2001/0001314 A1 | 5/2001 | Davison et al. |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0156521 A1 | 10/2002 | Ryan et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0236411 A1 | 11/2004 | Sarac et al. |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075720 A1 | 4/2005 | Nguyen et al. |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0182483 A1 | 8/2005 | Osborne et al. |

(56) References Cited

U.S. PATENT DOCUMENTS

| | | |
|---|---|---|
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0025855 A1 | 2/2006 | Lashinski et al. |
| 2006/0025857 A1 | 2/2006 | Bergheim et al. |
| 2006/0047338 A1 | 3/2006 | Jenson et al. |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0074485 A1 | 4/2006 | Realyvasques |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0149360 A1 | 7/2006 | Schwammenthal et al. |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |

(56) References Cited

U.S. PATENT DOCUMENTS

| | | |
|---|---|---|
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/47136 | 8/2000 |
| WO | 01/35870 | 5/2001 |
| WO | 01/47438 | 7/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 04/019825 | 3/2004 |
| WO | 04/089250 | 10/2004 |
| WO | 05/004753 | 1/2005 |
| WO | 2005/002466 | 1/2005 |
| WO | 05/046528 | 5/2005 |
| WO | 06/026371 | 3/2006 |
| WO | 2006/070372 | 7/2006 |
| WO | 08/047354 | 4/2008 |
| WO | 08/138584 | 11/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |
| WO | 09/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal Sep. 22, 2001, p. 355.

Boudjemline, et al., "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

(56) References Cited

OTHER PUBLICATIONS

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Ma, Ling, et al., "Double-crowned valved stents for off-pump mitral valve replacement," European Journal of Cardio Thoracic Surgery, 28:194-198, 2005.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Stassano et al., "Mid-term results of the valve-on-valve technique for bioprosthetic failure," Eur. J. Cardiothorac. Surg. 2000; 18:453-457.

Pavcnik et al., "Aortic and venous valve for percutaneous insertion," Min. Invas. Ther. & Allied Techol. 2000, vol. 9, pp. 287-292.

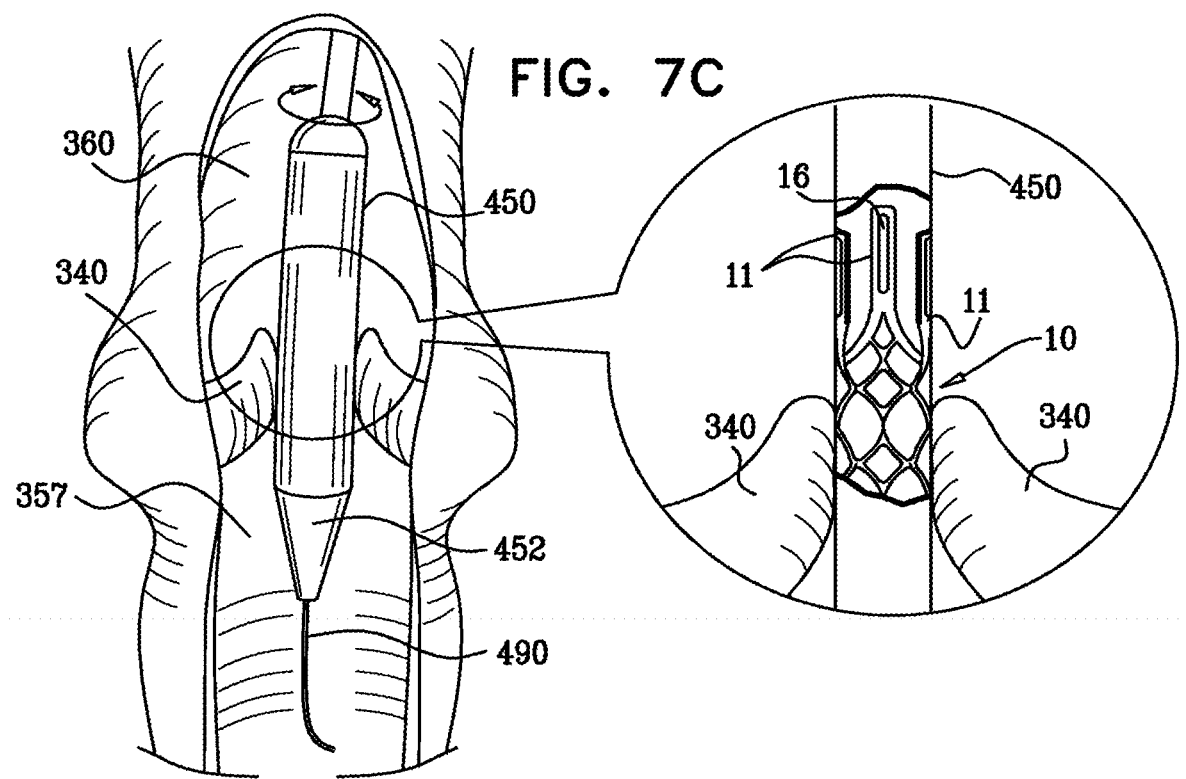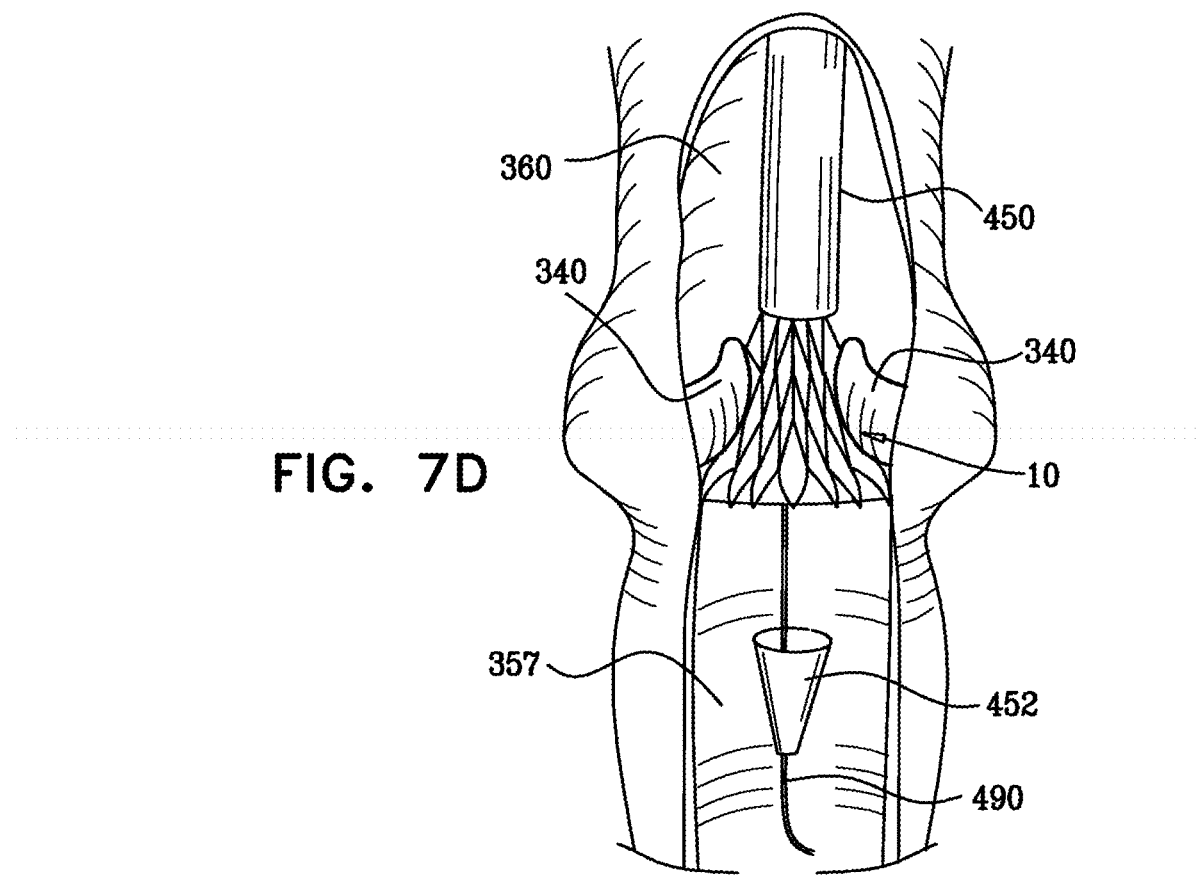

PROSTHETIC HEART VALVE HAVING IDENTIFIERS FOR AIDING IN RADIOGRAPHIC POSITIONING

CROSS-REFERENCE TO RELATED APPLICATIONS

This application is a Continuation of and claims priority to U.S. patent application Ser. No. 14/641,545, filed Mar. 9, 2015, now allowed, which is a Division of and claims priority to U.S. patent application Ser. No. 12/559,945, filed Sep. 15, 2009, now U.S. Pat. No. 8,998,981, which claims the benefit under 35 U.S.C. § 119(c) of U.S. Patent Application No. 61/192,201, filed Sep. 15, 2008, which are incorporated by references in their entirety.

FIELD OF THE INVENTION

The present invention relates generally to prosthetic heart valves, and specifically to techniques for accurately positioning such valves during implantation procedures.

BACKGROUND

Aortic valve replacement in patients with severe valve disease is a common surgical procedure. The replacement is conventionally performed by open heart surgery, in which the heart is usually arrested and the patient is placed on a heart bypass machine. In recent years, prosthetic heart valves have been developed which are implanted using minimally invasive procedures such as transapical or percutaneous approaches. These methods involve compressing the prosthesis radially to reduce its diameter, inserting the prosthesis into a delivery tool, such as a catheter, and advancing the delivery tool to the correct anatomical position in the heart. Once properly positioned, the prosthesis is deployed by radial expansion within the native valve annulus.

While these techniques are substantially less invasive than open heart surgery, the lack of line-of-sight visualization of the prosthesis and the native valve presents challenges, because the physician cannot see the actual orientation of the prosthesis during the implantation procedure. Correct positioning of the prostheses is achieved using radiographic imaging, which yields a two-dimensional image of the viewed area. The physician must interpret the image correctly in order to properly place the prostheses in the desired position. Failure to properly position the prostheses sometimes leads to device migration or to improper functioning. Proper device placement using radiographic imaging is thus critical to the success of the implantation.

PCT Publication WO 05/002466 to Schwammenthal et al., which is assigned to the assignee of the present application and is incorporated herein by reference, describes prosthetic devices for treating aortic stenosis.

PCT Publication WO 06/070372 to Schwammenthal et al., which is assigned to the assignee of the present application and is incorporated herein by reference, describes a prosthetic device having a single flow field therethrough, adapted for implantation in a subject, and shaped so as to define a fluid inlet and a diverging section, distal to the fluid inlet.

US Patent Application Publication 2006/0149360 to Schwammenthal et al., which is assigned to the assignee of the present application and is incorporated herein by reference, describes a prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end. A distal portion of the diverging member has a larger cross-sectional area for fluid flow therethrough than a proximal portion thereof.

US Patent Application Publication 2005/0197695 to Stacchino et al., describes a cardiac-valve prosthesis adapted for percutaneous implantation. The prosthesis includes an armature adapted for deployment in a radially expanded implantation position, the armature including a support portion and an anchor portion, which are substantially axially coextensive with respect to one another. A set of leaflets is coupled to the support portion. The leaflets can be deployed with the armature in the implantation position. The leaflets define, in the implantation position, a flow duct that is selectably obstructable. The anchor portion can be deployed to enable anchorage of the cardiac-valve prosthesis at an implantation site.

The following patents and patent application publications, are set forth as background:
U.S. Pat. No. 6,312,465 to Griffin et al.
U.S. Pat. No. 5,908,451 to Yeo
U.S. Pat. No. 5,344,442 to Deac
U.S. Pat. No. 5,354,330 to Hanson
US Patent Application Publication 2004/0260389 to Case et al.
U.S. Pat. No. 6,730,118 to Spencer et al.
U.S. Pat. No. 7,018,406 to Seguin et al.
U.S. Pat. No. 7,018,408 to Bailey et al.
U.S. Pat. No. 6,458,153 and US Patent Application Publication 2003/0023300 to Bailey et al.
US Patent Application Publication 2004/0186563 to Lobbi
US Patent Application Publication 2003/0130729 to Paniagua et al.
US Patent Application Publication 2004/0236411 to Sarac et al.
US Patent Application Publication 2005/0075720 to Nguyen et al.
US Patent Application Publication 2006/0058872 to Salahieh et al.
US Patent Application Publication 2005/0137686 Salahieh et al.
US Patent Application Publication 2005/0137690 to Salahieh et al.
US Patent Application Publication 2005/0137691 to Salahieh et al.
US Patent Application. Publication 2005/0143809 to Salahieh et al.
US Patent Application Publication 2005/0182483 to Osborne et al.
US Patent Application Publication 2005/0137695 to Salahieh et al.
US Patent Application Publication 2005/0240200 to Bergheim
US Patent Application Publication 2006/0025857 to Bergheim et al.
US Patent Application Publication 2006/0025855 to Lashinski et al.
US Patent Application Publication 2006/0047338 to Jenson et al.
US Patent Application Publication 2006/0052867 to Revuelta et al.
US Patent Application Publication 2006/0074485 to Realyvasquez
US Patent Application Publication 2006/0259136 to Nguyen et al.

U.S. Pat. No. 7,137,184 to Schreck
U.S. Pat. No. 6,296,662 to Caffey

SUMMARY

In some embodiments of the present invention, a prosthetic heart valve prosthesis comprises three commissural posts to which are coupled a prosthetic valve. The commissural posts are shaped so as define therethrough respective openings that serve as radiographic identifiers during an implantation procedure. During the procedure, the valve prosthesis, including the commissural posts, is initially collapsed within a delivery tube. Before expanding the valve prosthesis, a physician uses radiographic imaging, such as x-ray fluoroscopy, to provide visual feedback that aids the physician in rotationally aligning the commissural posts with respective native commissures of a native semilunar valve. The identifiers strongly contrast with the rest of the commissural posts and the valve prosthesis, which comprise a radiopaque material. Without such identifiers, it is generally difficult to three-dimensionally visually distinguish the commissural posts from one another and from the rest of the valve prosthesis, because the radiographic imaging produces a two-dimensional representation of the three-dimensional valve prosthesis. When the valve prosthesis is in a collapsed state, the elements thereof overlap in a two-dimensional image and are generally indistinguishable.

In some embodiments of the present invention, the physician selects one of the commissural posts having a radiographic identifier, and attempts to rotationally align the selected post with one of the native commissures, such as the commissure between the left and right coronary sinuses. Because the radiographic image is two-dimensional, all of the posts appear in the image as though they are in the same plane. The physician thus cannot distinguish between two possible rotational positions of the posts: (1) the desired rotational position, in which the selected post faces the desired native commissure, and (2) a rotational position 180 degrees from the desired rotational position, in which the selected post faces the side of the native valve opposite the desired native commissure. For example, if the desired native commissure is the commissure between the left and right coronary sinuses, in position (2) the post is rotationally aligned with the noncoronary sinus, although this undesired rotation is not apparent in the radiographic image.

To ascertain whether the posts are in rotational Position (1) or (2), the physician slightly rotates the valve prosthesis. If the radiographic identifier on the selected post appears to move in the radiographic image in the same direction as the rotation, the selected post is correctly rotationally aligned in the desired position (1). If, on the other hand, the radiographic identifier appears to move in the direction opposite the direction of rotation, the selected post is incorrectly rotationally aligned in position (2). To correct the alignment, the physician may rotate the valve prosthesis approximately 60 degrees in either direction, thereby ensuring that one of the two other posts is now rotationally aligned in position (1). (The valve prosthesis typically has three-fold rotational symmetry, such that rotation of 60 degrees is sufficient to properly align one of the posts with the selected native commissure, and the prosthesis need not be rotated a full 180 degrees.) In these embodiments, the openings through the posts that define the radiographic identifiers may assume any convenient shape, such as a slit.

In some embodiments of the present invention, the openings that define the radiographic identifiers are shaped to be reflection-asymmetric along respective post axes that are generally parallel with a central longitudinal axis of the prosthesis when the posts assume their collapsed position. For example, the identifiers may be shaped as one or more reflection-asymmetric characters, such as numbers or letters of the alphabet, e.g., B, C, D, E, etc. The physician can thus readily identify the true orientation of the selected post that appears to be rotationally aligned with the selected native commissure. If the identifier on the selected post appears in the correct left-right orientation, the selected post is aligned in the desired position (1). If, on the other hand, the identifier appears as the mirror image of its correct left-right orientation, the selected post is incorrectly rotationally aligned in position (2). To correct the alignment, the physician may rotate the valve prosthesis approximately 60 degrees in either direction, thereby ensuring that one of the two other posts is now rotationally aligned in position (1).

There is therefore provided, in accordance with an embodiment of the present invention, apparatus including a valve prosthesis, which includes a prosthetic heart valve, and three or more commissural posts, to which the prosthetic heart valve is coupled. The posts are arranged circumferentially around a central longitudinal axis of the valve prosthesis, and are configured to assume a collapsed position prior to implantation of the prosthesis, and an expanded position upon the implantation of the prosthesis. One or more of the commissural posts are provided with respective radiographic identifiers that are shaped to be reflection-asymmetric about respective post axes that are generally parallel with the central longitudinal axis when the posts assume the collapsed position.

For some applications, the radiographic identifiers have the shape of one or more reflection-asymmetric characters.

In an embodiment, the one or more of the commissural posts are shaped to define respective openings therethrough which define the respective radiographic identifiers. Alternatively, the radiographic identifiers include a material having a first radiopacity that is different from a second radiopacity of the commissural posts, which material is coupled to the one or more of the commissural posts.

For some applications, the valve prosthesis includes exactly three commissural posts.

There is further provided, in accordance with an embodiment of the present invention, a method including:
providing a valve prosthesis that includes a prosthetic heart valve, and three or more commissural posts, to which the prosthetic heart valve is coupled, which posts are arranged circumferentially around a central longitudinal axis of the valve prosthesis, and are configured to assume a collapsed position prior to implantation of the prosthesis, and an expanded position upon the implantation of the prosthesis, and at least one of which commissural posts is provided with a radiographic identifier;
while the posts assume the collapsed position, placing, via a blood vessel of the subject, the valve prosthesis at least partially in a heart of a subject in a vicinity of a native heart valve having native commissures;
generating a fluoroscopic image of the native commissures and valve prosthesis; and
rotationally aligning the at least one of the commissural posts with one of the native commissures using the radiographic identifier visible in the image.

In an embodiment, rotationally aligning includes rotating the valve prosthesis; observing whether the at least one of the commissural posts appears to move in the image in the same direction that the valve prosthesis is rotated, or in an opposite direction; and, if the at least one of the commissural posts appears to move in the image. in the opposite direction, rotating the valve prosthesis to correct. a rotational alignment of the valve prosthesis.

For some applications, the valve prosthesis includes exactly three commissural posts, and is configured to have three-fold rotational symmetry, and rotating the valve prosthesis to correct the rotational alignment includes rotating the valve prosthesis approximately 60 degrees.

In an embodiment, the radiographic identifier is shaped to be reflection-asymmetric about a post axis of the at least one of the commissural posts, which axis is generally parallel with the central longitudinal axis when the posts assume the collapsed position. For some applications, the radiographic identifier has the shape of a reflection-asymmetric character.

For some applications, rotationally aligning includes observing in the image whether the radiographic identifier appears in a correct left-right orientation, and, if the radiographic identifier does not appear in the correct left-right orientation, rotating the valve prosthesis to correct a rotational alignment of the valve prosthesis. For some applications, the valve prosthesis includes exactly three commissural posts, and is configured to have three-fold rotational symmetry, and rotating the valve prosthesis to correct the rotational alignment includes rotating the valve prosthesis approximately 60 degrees.

In an embodiment, the at least one of the commissural posts is shaped to define an opening therethrough which defines the radiographic identifier. Alternatively, the radiographic identifier includes a material having a first radiopacity that is different from a second radiopacity of the at least one of the commissural posts, which material is coupled to the at least one of the commissural posts.

For some applications, the one of the native commissures is a native commissure ($C_{RL}$) between a left coronary sinus and a right coronary sinus, and rotationally aligning includes rotationally aligned the one of the commissural posts with the $C_{RL}$.

There is still further provided, in accordance with an embodiment of the present invention, a method including:

providing a valve prosthesis that includes a prosthetic heart valve, and three or more commissural posts, to which the prosthetic heart valve is coupled, which posts are arranged circumferentially around a central longitudinal axis of the valve prosthesis, and are configured to assume a collapsed position prior to implantation of the prosthesis, and an expanded position upon the implantation of the prosthesis;

while the posts assume the collapsed position, placing, via a blood vessel of the subject, the valve prosthesis at least partially in a heart of a subject in a vicinity of a native heart valve having native commissures;

generating a fluoroscopic image of the native commissures and valve prosthesis; and rotationally aligning the at least one of the commissural posts with one of the native commissures by:

rotating the valve prosthesis, observing whether the at least one of the commissural posts appears to move in the image in the same direction that the valve prosthesis is rotated, or in an opposite direction, and if the at least one of the commissural posts appears to move in the image in the opposite direction, rotating the valve prosthesis to correct a rotational alignment of the valve prosthesis.

For some applications, the valve prosthesis includes exactly three commissural posts, and is configured to have three-fold rotational symmetry, and rotating the valve prosthesis to correct the rotational alignment includes rotating the valve prosthesis approximately 60 degrees.

There is additionally provided, in accordance with an embodiment of the present invention, apparatus including a valve prosthesis, which includes:

a prosthetic heart valve;

a support structure, which includes a first material having a first radiopacity; and one or more radiographic identifiers, which include a second material having a second radiopacity different from the first radiopacity, and which are coupled to the support structure at respective locations.

In an embodiment, the radiographic identifiers are shaped to be reflection-asymmetric about respective identifier axes that are generally parallel with a central longitudinal axis of the valve prosthesis.

For some applications, the identifiers are arranged circumferentially around a central longitudinal axis of the valve prosthesis.

For some applications, the support structure is shaped so as to define a bulging proximal skirt, and the identifiers are coupled to the skirt.

For some applications, the support structure includes three or more commissural posts, to which the prosthetic heart valve is coupled, which posts are arranged circumferentially around a central longitudinal axis of the valve prosthesis, the locations at which the identifiers are coupled to the support structure are not on the posts, and the locations are radially aligned with the posts.

For some applications, the support structure includes three or more commissural posts, to which the prosthetic heart valve is coupled, which posts are arranged circumferentially around a central longitudinal axis of the valve prosthesis, and the locations at which the identifiers are coupled to the support structure are on the posts.

The present invention will be more fully understood from the following detailed description of embodiments thereof, taken together with the drawings, in which:

BRIEF DESCRIPTION OF THE DRAWINGS

FIGS. 7C-7E are schematic illustrations of an implantation procedure of an alternative configuration of the valve prosthesis of FIG. 1, in accordance with an embodiment of the present invention;

DETAILED DESCRIPTION

Figure 1:
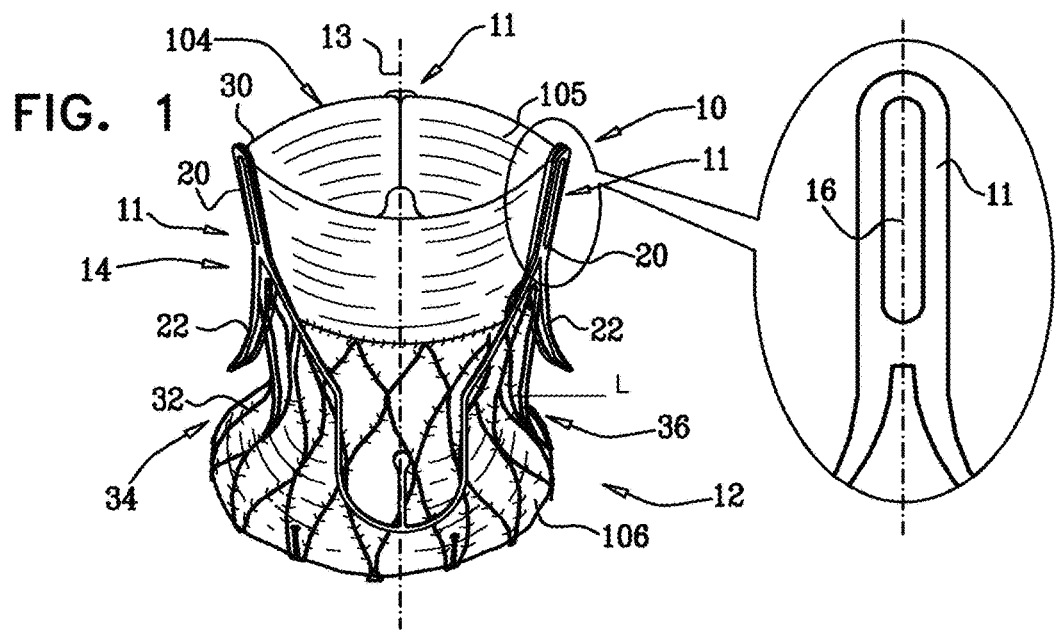
FIG. 1 is a schematic illustration of a fully-assembled valve prosthesis, in accordance with an embodiment of the present invention.

FIG. 1 is a schematic illustration of a fully-assembled valve prosthesis 10, in accordance with an embodiment of the present invention. Typically, valve prosthesis 10 comprises exactly three commissural posts 11, arranged circumferentially around a central longitudinal axis 13 of valve prosthesis 10. Valve prosthesis 10 further comprises a prosthetic distal valve 104 coupled to couple to commissural posts 11. Valve 104 typically comprises a pliant material 105. Pliant material 105 of valve 104 is configured to collapse inwardly (i.e., towards central longitudinal axis 13) during diastole, in order to inhibit retrograde blood flow, and to open outwardly during systole, to allow blood flow through the prosthesis. For some applications, valve prosthesis 10 comprises a collapsible inner support structure 12 that serves as a proximal fixation member, and a collapsible outer support structure 14 that serves as a distal fixation member.

One or more (e.g., all) of commissural posts 11 are shaped so as define therethrough respective openings 16 that serve as radiographic identifiers during an implantation procedure, as described herein below with reference to FIGS. 3-8B. The openings may assume any convenient, shape, for example, slits, as shown in FIGS. 1, 2A-B, and 6A-B. In some embodiments, the openings are shaped to be reflection-asymmetric along respective post axes generally parallel with central longitudinal axis 13 of prosthesis 10 when the posts assume their collapsed position, as described herein below with reference to FIGS. 10A-B. For some applications, in addition to serving as the radiographic identifiers, openings 16 are used for coupling valve 104 to support structures 12 and 14. Although pliant material 105 of valve 104 at least partially fills openings 16, the material is substantially more radiolucent than commissural posts 11, and thus does not reduce the radiographic visibility of the radiographic identifiers. Alternatively, one or more of posts 11 do not necessarily define openings 16, and the one or more posts instead comprise radiographic identifiers comprising a material having a radiopacity different from (greater or less than) the radiopacity of posts 11, such as gold or tantalum.

Valve prosthesis 10 is configured to be placed in a native diseased valve of a subject, such as a native stenotic aortic or pulmonary valve, using a minimally-invasive approach, such as a beating heart transapical procedure, such as described herein below with reference to FIG. 7A, or a retrograde transaortic procedure, such as described herein below with reference to FIG. 7B. As used in the present application, including in the claims, a "native semilunar valve" is to be understood as including: (a) native semilunar valves that include their native leaflets, and (b) native semilunar valves, the native leaflets of which have been surgically excised or are otherwise absent.

Figure 2A:
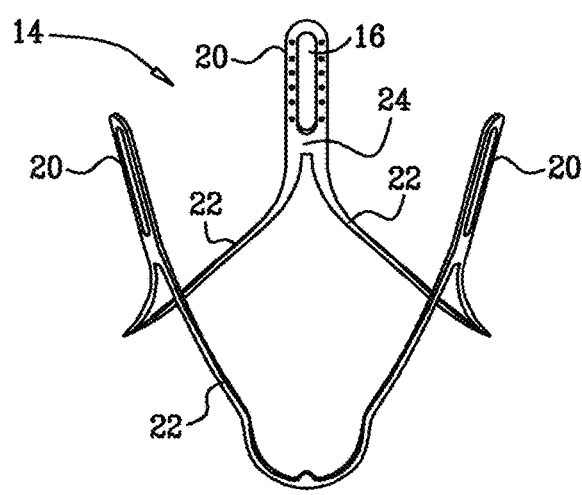
FIGS. 2A and 2B are schematic illustrations of a collapsible outer support structure and a collapsible inner support structure, respectively, prior to assembly together into the valve prosthesis of FIG. 1, in accordance with an embodiment of the present invention.
Figure 2B:
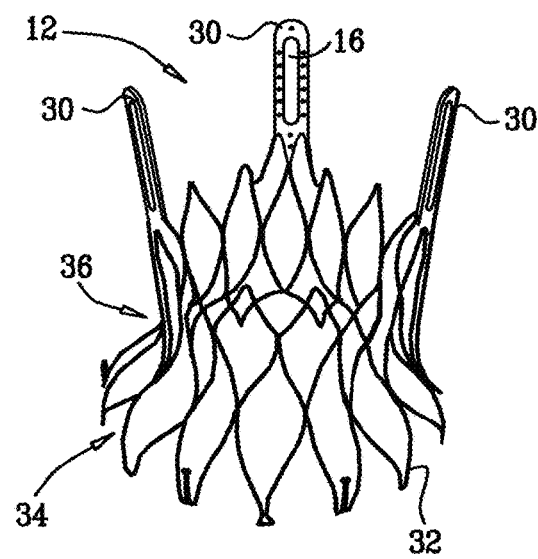

Reference is made to FIG. 2A, which is a schematic illustration of collapsible outer support structure 14 prior to assembly with inner support structure 12, in accordance with an embodiment of the present invention. In this embodiment, outer support structure 14 is shaped so as to define a plurality of distal diverging strut supports 20, from which a plurality of proximal engagement arms 22 extend radially outward in a proximal direction. Engagement arms 22 are typically configured to be at least partially disposed within aortic sinuses of the subject, and, for some applications, to engage and/or rest against floors of the aortic sinuses, and to apply an axial force directed toward a left ventricle of the subject. Outer support structure 14 comprises a suitable material that allows mechanical deformations associated with crimping and expansion of valve prosthesis 10, such as, but not limited to, nitinol or a stainless steel alloy (e.g., AISI 316).

Reference is made to FIG. 23, which is a schematic illustration of collapsible inner support structure 12 prior to assembly with outer support structure 14, in accordance with an embodiment of the present invention. For some applications, inner support structure 12 is shaped so as to define a plurality of distal diverging inner struts 30, and a bulging proximal skirt 32 that extends from the struts. A proximal portion 34 of proximal skirt 32 is configured to engage a left ventricular outflow tract (LVOT) of the subject and/or periannular tissue at the top of the left ventricle. A relatively narrow throat section 36 of proximal skirt 32 is configured to be positioned at a valvular annulus of the subject, and to engage the native valve leaflets. Inner support structure 12 comprises, for example, nitinol, a stainless steel alloy, another metal, or another biocompatible material.

Reference is again made to FIG. 1. Inner and outer support structures 12 and 14 are assembled together by placing outer support structure 14 over inner support structure 12, such that cuter strut supports 20 are aligned with, and typically support, respective inner struts 30, and engagement arms 22 are placed over a portion of proximal skirt 32. Inner struts 30 and outer strut supports 20 together define commissural posts 11.

Although exactly three commissural posts 11 are shown in the figures, for some applications valve prosthesis 10 comprises fewer or more posts 11, such as two posts 11, or four or more posts 11.

Typically, valve prosthesis 10 further comprises a graft covering 106 which is coupled to proximal skirt 32, such as by sewing the covering within the skirt (configuration shown in FIG. 1) or around the skirt (configuration not shown). Inner support structure 12 thus defines a central structured body for flow passage that proximally terminates in a flared inlet (proximal skirt 32) that is configured to be seated within an LVOT immediately below an aortic annulus/aortic valve. For some applications, graft covering 106 is coupled at one or more sites to pliant material 105.

In an embodiment of the present invention, a portion valve prosthesis 10 other than commissural posts 11, e.g., proximal skirt. 32, is shaped so as to define openings 16 that serve as radiographic identifiers. Alternatively or additionally, the commissural posts or this other portion of the prosthesis comprise radiographic identifiers comprising a material having a radiopacity different from (greater or less than) the radiopacity of other portions of the prosthesis. For some applications, the radiographic identifiers are radially aligned with commissural posts 11.

Figure 3:
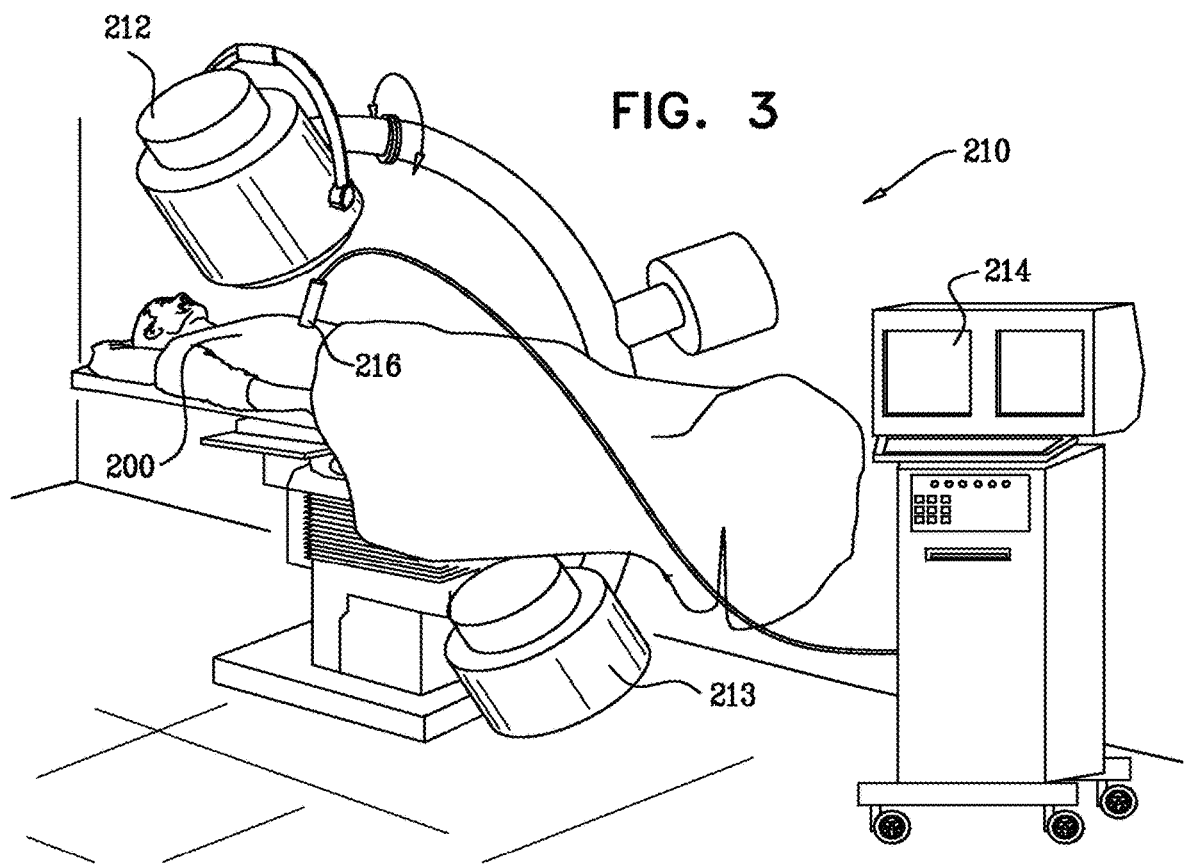
FIG. 3 is a schematic illustration of a subject undergoing a transapical or percutaneous valve replacement procedure, in accordance with an embodiment of the present invention.

FIG. 3 is a schematic illustration of a subject 200 undergoing a transapical or percutaneous valve replacement procedure, in accordance with an embodiment of the present invention. A fluoroscopy system 210 comprises a fluoroscopy source 213, a fluoroscopy detector 212, and a monitor 214. Fluoroscopy source 213 is positioned over subject 200 so as to obtain a left anterior oblique (LAO) projection of between 30 and 45, such as between 30 and 40, degrees with a 30-degree cranial tilt (for orthogonal projection of the annulus). Typically, imaging is enhanced using an ultrasound probe 216.

Figure 4:
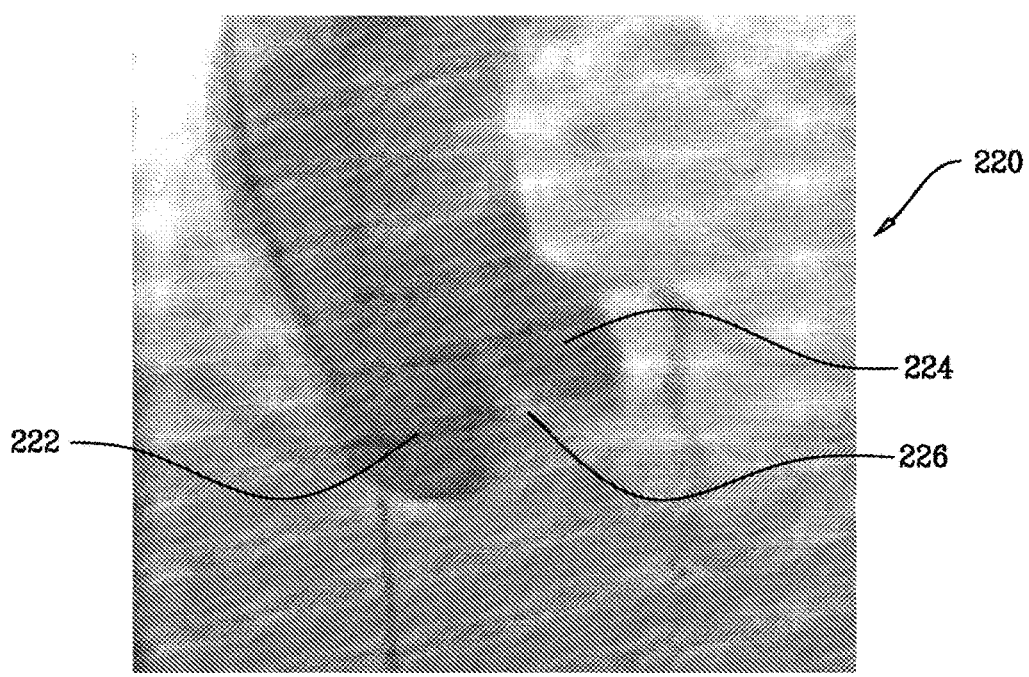
FIG. 4 shows an exemplary fluoroscopic view generated with a fluoroscopic system during a valve replacement procedure, in accordance with an embodiment of the present invention.

FIG. 4 shows an exemplary fluoroscopic view 220 generated with fluoroscopic system 210 during a valve replacement procedure, in accordance with an embodiment of the present invention. In the view, a right coronary sinus (RCS) 222 and a left coronary sinus (LCS) 224 are visible, as are the respective coronary arteries that originate from the sinuses. The view also shows a commissure 226 between the right and left sinuses ($C_{RL}$). RCS 222, LCS 224, and $C_{RL}$ 226 serve as clear anatomical landmarks during the replacement procedure, enabling the physician to readily ascertain the layout of the aortic root.

Figure 5:
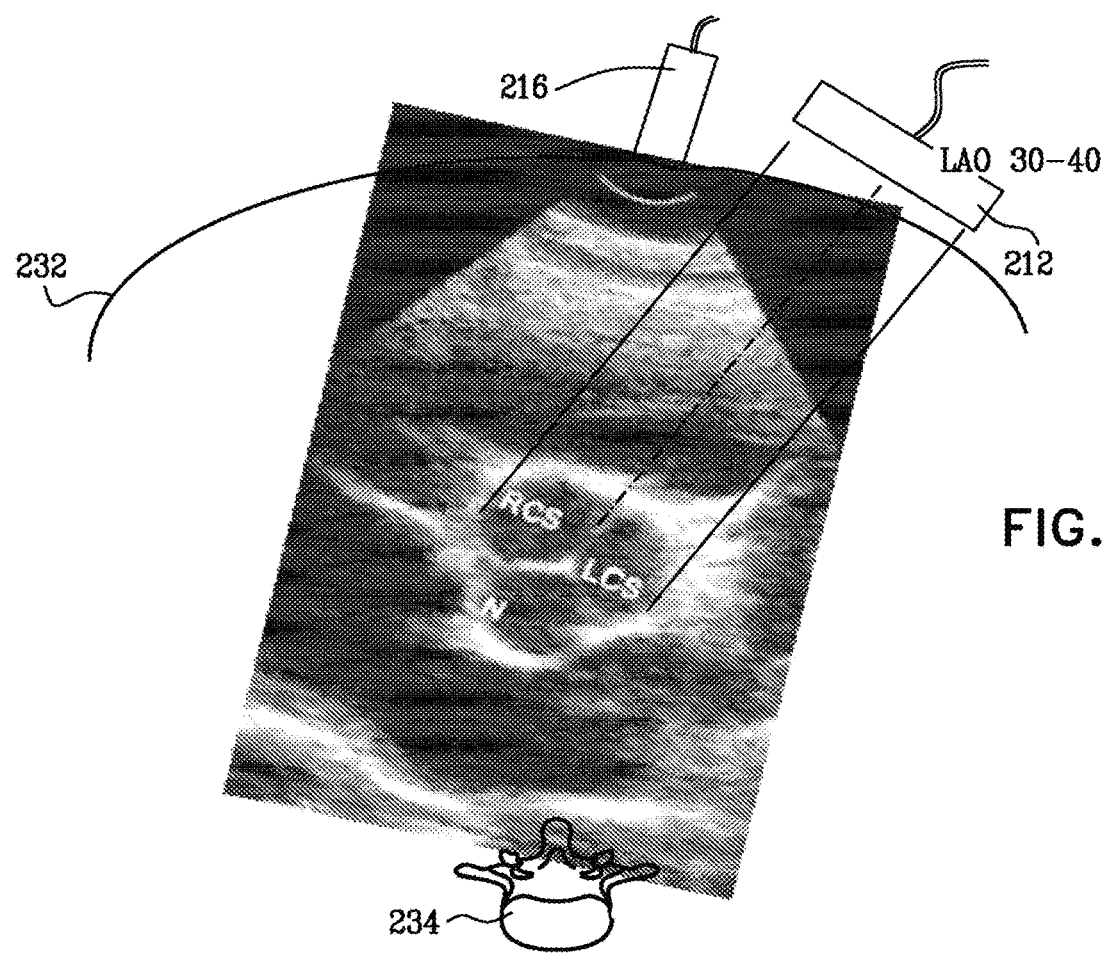
FIG. 5 shows an exemplary ultrasound view generated with an ultrasound probe during a valve replacement procedure, in accordance with an embodiment of the present invention.

FIG. 5 shows an exemplary ultrasound view 230 generated with ultrasound probe 216 during a valve replacement procedure, in accordance with an embodiment of the present invention. In the view, the RCS, LCS, and non-coronary sinus (N) are visible. The orientation of view 230 can be seen with respect to a sternum 232 and a spine 234, as well as with respect to fluoroscopy detector 212.

Figure 6A:
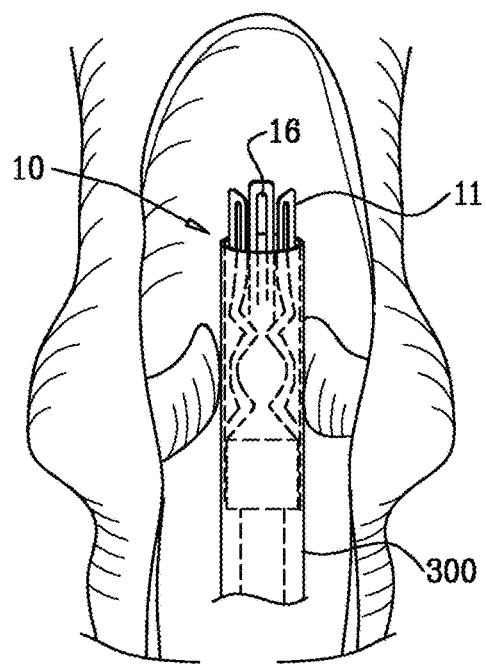
FIGS. 6A and 6B are schematic and fluoroscopic views, respectively, of the valve prosthesis of FIG. 1 in a collapsed position in a catheter, in accordance with an embodiment of the present invention.
Figure 6B:
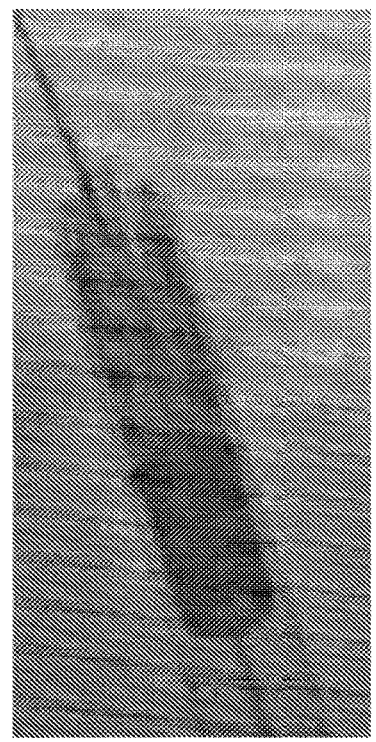

FIGS. 6A and 6B are schematic and fluoroscopic views, respectively, of valve prosthesis 10 in a collapsed position in a catheter 300, in accordance with an embodiment of the present invention. In this embodiment, openings 16 are shaped as slits. As can be seen in FIG. 613, these slits are clearly visible with fluoroscopy.

Figure 7A:
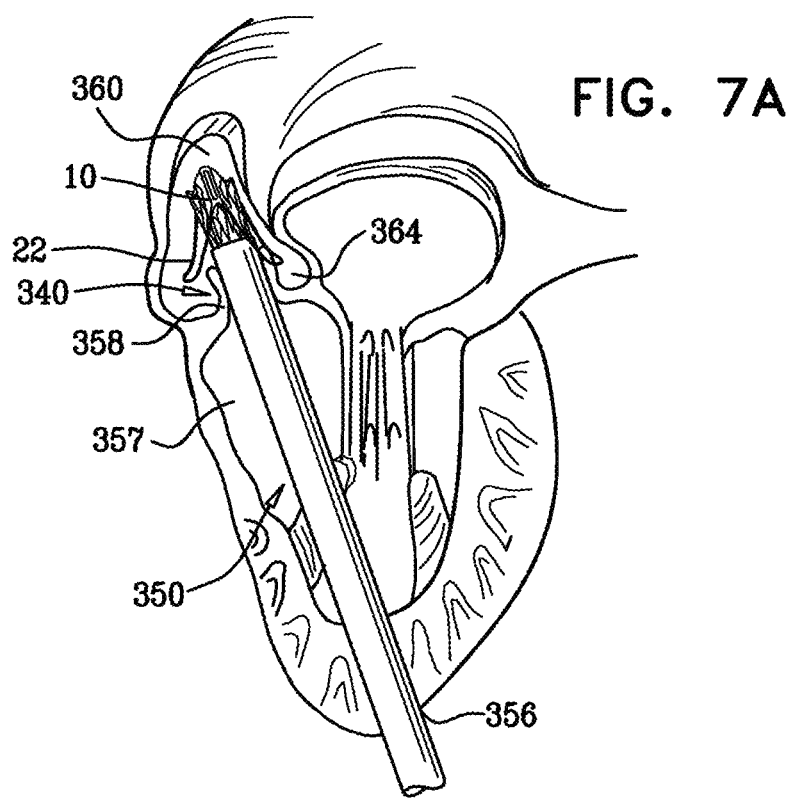
FIGS. 7A and 7B are schematic illustrations of the valve prosthesis of FIG. 1 in situ upon completion of transapical and retrograde transaortic implantation procedures, respectively, in accordance with respective embodiments of the present invention.
Figure 7B:
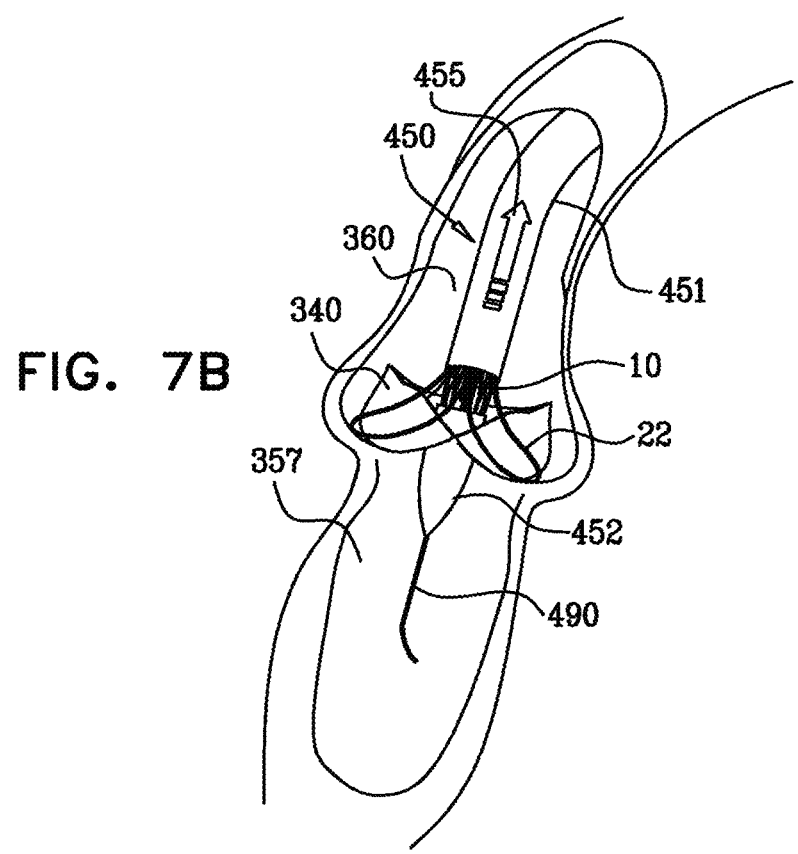

Reference is made to FIGS. 7A and 7B, which are schematic illustrations of valve prosthesis 10 in situ upon completion of transapical and retrograde transaortic implantation procedures, respectively, in accordance with respective embodiments of the present invention.

In the transapical procedure, as shown in FIG. 7A, an introducer overtube or trocar 150 is inserted into a left ventricular apex 156 using a Seldinger technique. Through this trocar, a delivery catheter (not shown in the figure) onto which collapsed valve prosthesis 10 is mounted, is advanced into a left ventricle 357 where its motion is terminated, or through left ventricle 357 until the distal end of a dilator (not shown) passes native aortic valve leaflets 358. For example, apex 356 may be punctured using a standard Seldinger technique, and a guidewire may be advanced into an ascending aorta 360. Optionally, a native aortic valve 340 is partially dilated to about 15-20 mm (e.g., about 16 mm), typically using a standard valvuloplasty balloon catheter. (In contrast, full dilation would be achieved utilizing dilation of 20 mm or more.) Overtube or trocar 350 is advanced into the ascending aorta. Overtube or trocar 350 is pushed beyond aortic valve 340 such that the distal end of overtube or trocar 350 is located above the highest point of native aortic valve 340. The dilator is removed while overtube or trocar 350 remains in place with its distal end located above aortic valve 340. Alternatively, the procedure may be modified so that overtube or trocar 350 is placed within left ventricle 350 and remains within the left ventricle throughout the entire implantation procedure. Valve prosthesis 10 is advanced through the distal end of overtube or trocar 350 into ascending aorta. 360 distal to native leaflets 358.

Valve prosthesis 10, typically while still within the catheter, is rotated to align arms 22 with aortic sinuses 364, as described herein below with reference to FIGS. 8A-B or FIGS. 10A-B. After the prosthesis is properly rotationally aligned, withdrawal of the catheter causes engagement arms 22 to flare out laterally to an angle which is typically predetermined by design, and to open in an upstream direction. Gentle withdrawal of the delivery catheter, onto which prosthesis 10 with flared-out arms 22 is mounted, causes the arms to slide into aortic sinuses 364. Release of the device from the delivery catheter causes a lower inflow portion of prosthesis 10 to unfold and press against the upstream side of native leaflets 358, thereby engaging with the upstream fixation arms in the aortic sinuses. The upstream fixation arms serve as counterparts to the lower inflow portion of the prosthesis in a mechanism that locks the native leaflets and the surrounding periannular tissue for fixation.

For some applications, prosthesis 10 is implanted using techniques described with reference to FIGS. 5A-C in U.S. application Ser. No. 12/050,628, filed Mar. 18, 2008, entitled, "Valve suturing and implantation procedures," which is incorporated herein by reference.

In the retrograde transaortic procedure, as shown in FIG. 7B, valve prosthesis 10 is positioned in a retrograde delivery catheter 450. A retrograde delivery catheter tube 451 of catheter 450 holds engagement arms 22, and a delivery catheter cap 452 holds proximal skirt 32 (not shown). A guidewire 490 is transaortically inserted into left ventricle 357. Optionally, stenotic aortic valve 340 is partially dilated to about 15-20 mm (e.g., about 16 mm), typically using a standard valvuloplasty balloon catheter. Retrograde delivery catheter 450 is advanced over guidewire 490 into ascending aorta 360 towards native aortic valve 340. Retrograde delivery catheter 450 is advanced over guidewire 490 until delivery catheter cap 452 passes through native aortic valve 340 partially into left ventricle 357.

Valve prosthesis 10, typically while still within the catheter, is rotated to align arms 22 with aortic sinuses 364, as described herein below with reference to FIGS. 8A-B or FIGS. 1A-B. Retrograde delivery catheter tube 451 is pulled back (in the direction indicated schematically by an arrow 455), while a device stopper (not shown) prevents valve prosthesis 10 within tube 451 from being pulled back with tube 451, so that engagement arms 22 are released and flare out laterally into the sinuses. At this stage of the implantation procedure, proximal skirt 32 of prosthesis 10 remains in delivery catheter cap 452.

Delivery catheter cap 452 is pushed in the direction of the apex of the heart, using a retrograde delivery catheter cap shaft (not shown) that passes through tube 451 and prosthesis 10. This advancing of cap 452 frees proximal skirt 32 to snap or spring open, and engage the inner surface of the LVOT. Retrograde delivery catheter tube 451 is further pulled back until the rest of valve prosthesis 10 is released from the tube. Retrograde delivery catheter tube 451 is again advanced over the shaft toward the apex of the heart, until tube 451 rejoins cap 452. Retrograde delivery catheter 450 and guidewire 490 are withdrawn from left ventricle 357, and then from ascending aorta 360, leaving prosthesis 10 in place.

For some applications, prosthesis 10 is implanted using techniques described with reference to FIGS. 9A-G in above-mentioned U.S. application Ser. No. 12/050,628.

Figure 7E:
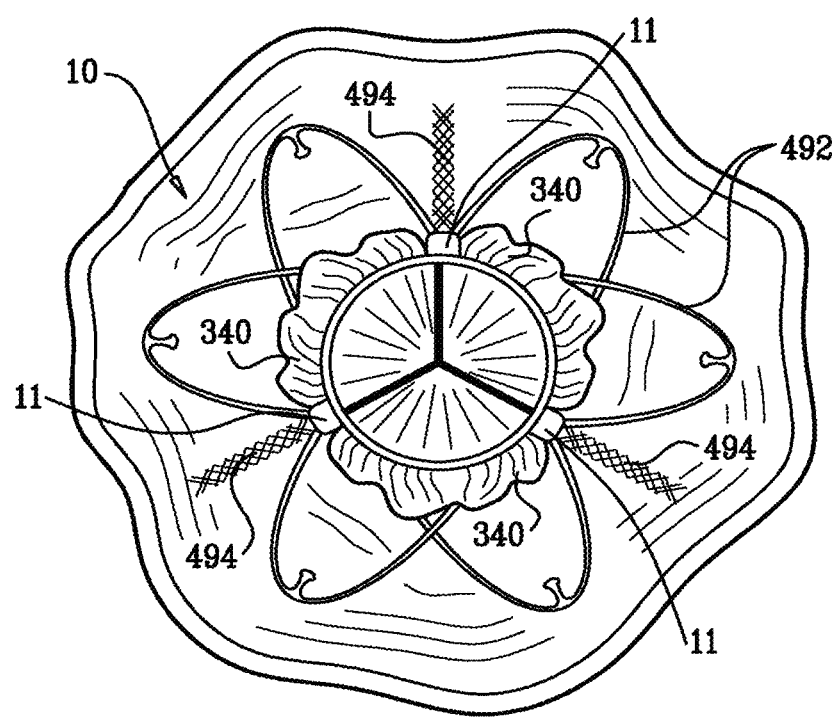

Reference is made to FIGS. 7C-7E, which are schematic illustrations of an implantation procedure of an alternative configuration of valve prosthesis 10, in accordance with an embodiment of the present invention. In this configuration, valve prosthesis 10 does not comprise proximal engagement arms 22. Even without these arms, which rest in the sinus floors and thus may aid in properly rotationally aligning the prosthesis, the techniques described herein achieve proper alignment of the prosthesis. For some applications, valve prosthesis 10 is configured as described in a US provisional patent application filed on even date herewith, entitled, "Prosthetic heart valve for transfemoral delivery," which is assigned to the assignee of the present application and is incorporated herein by reference.

FIG. 7C shows valve prosthesis 10 positioned in retrograde delivery catheter 450, which is advanced into left ventricle 357 over guidewire 490. Valve prosthesis 10, typically while still within the catheter, is rotated to align commissural posts 11 with the native commissures, as described herein below with reference to FIGS. 8A-B or FIGS. 10A-B. After the prosthesis is properly rotationally aligned, withdrawal of the catheter causes expansion of the frame of prosthesis, as shown in FIG. 7D. FIG. 7E shows this configuration of prosthesis 10 positioned within the aortic root (viewed from the aorta). The frame of the prosthesis is shaped so as to define distal support members 492, which extend in a downstream direction (i.e., they do not extend into the floors of the aortic sinuses). Distal support elements 492 are configured to rest against the downstream portion of the aortic sinuses upon implantation of valve prosthesis 10, so as to provide support against tilting of the prosthesis with respect to a central longitudinal axis of the prosthesis. As can be seen in FIG. 7E, commissural posts 11 of the valve prosthesis are rotationally aligned with native commissures 494.

Figure 8A:
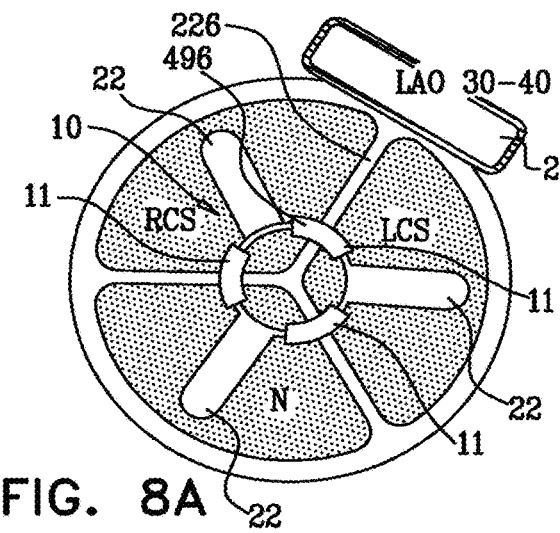
FIGS. 8A-B are schematic illustrations of the valve prosthesis of FIG. 1 positioned within the aortic root, in accordance with an embodiment of the present invention.
Figure 8B:
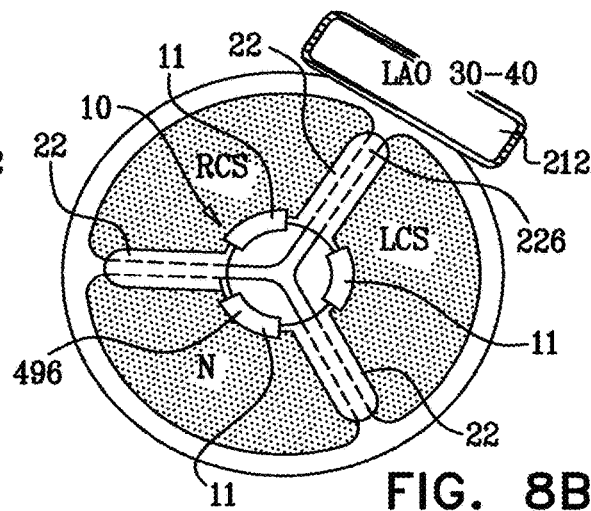

Reference is made to FIGS. 8A-B, which are schematic illustrations of valve prosthesis 10 positioned within the aortic root (viewed from the aorta), in accordance with an embodiment of the present invention. As described above with reference to FIGS. 7A-B, during an implantation procedure, a delivery catheter is inserted into an overtube and advanced until the distal end of commissural posts 11 arrive near the end of the overtube.

For configurations of valve prosthesis 10 that include proximal engagement arms 22, the arms are still within the catheter. To properly rotationally align pests with the native commissures, the physician rotates valve prosthesis 10 under fluoroscopy until one 496 of commissural posts 11 is aligned with one of the native commissures, such as commissure 226 between the right and left sinuses ($C_{RL}$). In an attempt to achieve such a rotational position, the physician rotates the prosthesis until one of openings 16 that serve as radiographic identifiers is centered from the viewpoint of the fluoroscopic LAO projection such as shown in FIG. 6B (openings 16 are not visible from the view of FIGS. 8A-B). The other two commissural posts 11 flank the centered post.

At this stage of the procedure, because the radiographic image is two-dimensional and all of the posts appear in the image as though they are in the same plane, it is difficult for the physician to ascertain whether commissural post 496 selected for alignment is:

(1) in the desired rotational position, closer to fluoroscopy detector 212 (FIG. 3) than are the other two commissures, and thus properly aligned with the $C_{RL}$ 226, as shown in FIG. 8A; or
(2) farther away from the fluoroscopy detector than are the other two posts, rotated 180 degrees from the desired rotational position, as shown in FIG. 8B. In this rotational orientation, centered post 496 projects itself onto $C_{RL}$ 226, but actually faces the noncoronary sinus (N) away from the fluoroscopy detector, such that valve prosthesis 10 is misaligned by 60 degrees (because the prosthesis typically has three-fold rotational symmetry).

Figure 9:
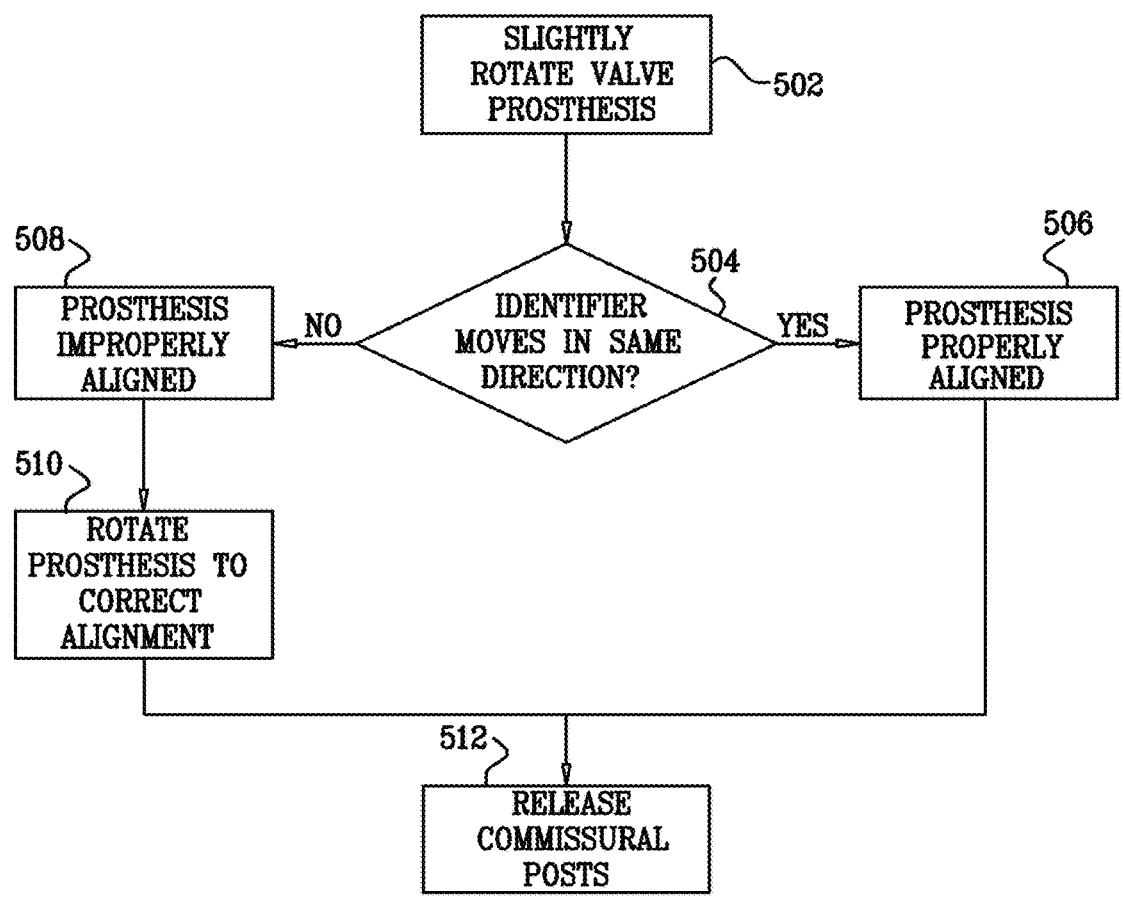
FIG. 9 is a flow chart that schematically illustrates a method for ascertaining whether the valve prosthesis of FIG. 1 or FIGS. 7C-E are properly rotationally aligned with the native commissures, in accordance with an embodiment of the present invention

Reference is made to FIG. 9, which is a flow chart that schematically illustrates a method 500 for ascertaining whether the posts are in the first or second possible rotational position, in accordance with an embodiment of the present invention. At an initial rotation step 502, the physician slightly rotates valve prosthesis 10. At an apparent rotation check step 504, the physician ascertains whether the radiographic identifier on the selected post appears to move in the radiographic image in the same direction as the rotation. If the identifier appears to move in the same direction as the rotation, the physician ascertains that the selected post is correctly rotationally aligned in the desired position (1) (after the physician slightly rotates the prosthesis in the opposite direction to return it to its initial position), at a proper alignment ascertainment step 506. If, on the other hand, the radiographic identifier appears to move in the direction opposite the direction of rotation, the physician ascertains that the selected post is incorrectly rotationally aligned in position (2), at an improper alignment ascertainment step 508. To correct the alignment, the physician rotates the valve prosthesis approximately 60 degrees in either direction, thereby ensuring that one of the two other posts is now rotationally aligned in position (1), at an alignment correction step 510. (The valve prosthesis typically has three-fold rotational symmetry, such that rotation of 60 degrees is sufficient to properly align one of the posts with the selected native commissure, and the prosthesis need not be rotated a full 180 degrees.) For example, assume that at initial rotation step 502 the physician rotates the prosthesis clockwise, as viewed from the aorta. If the valve prosthesis is properly aligned, the radiographic identifier on the selected post appears to move toward the LCS at apparent rotation check step 504. Once the valve prosthesis is properly aligned, commissural posts 11 are released from the catheter, as well as proximal engagement arms 22, for configurations of the prosthesis that include such arms, at a commissural post release step 512. In these embodiments, openings 16 through posts 11 that define the radiographic identifiers may assume any convenient shape, such as a slit.

In an embodiment of the present invention, this technique for rotationally aligning posts 11 with the native commissures is used for aligning a valve prosthesis that does not include radiographic identifiers. Instead of using such identifiers, the physician observes elements of the prosthesis that are discernible in the radiographic images, such as posts 11.

Figure 10A:
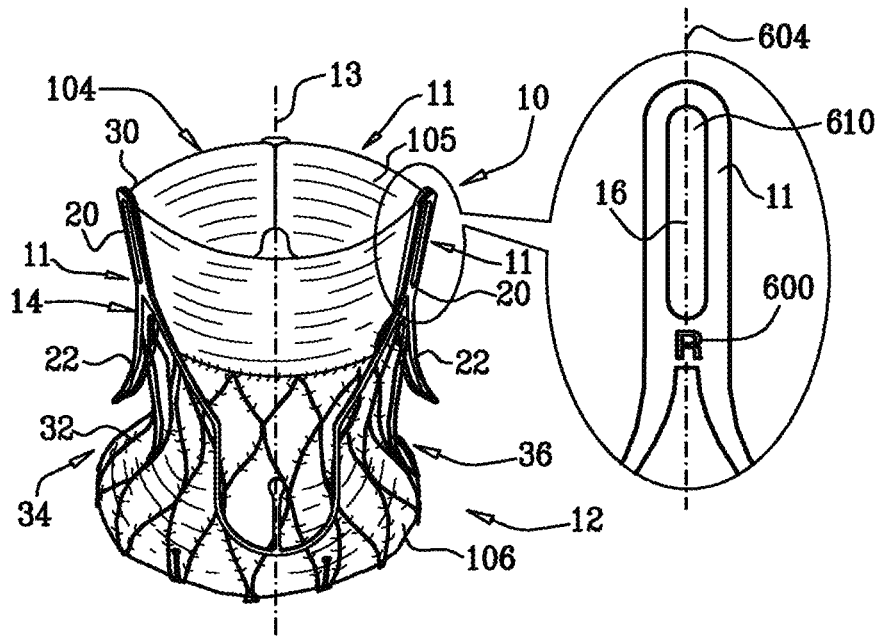
FIGS. 10A and 10B are schematic illustrations of reflection-asymmetric radiographic identifiers on commissural posts of the valve prosthesis of FIG. 1 or FIGS. 7C-E, in accordance with respective embodiments of the present invention.
Figure 10B:
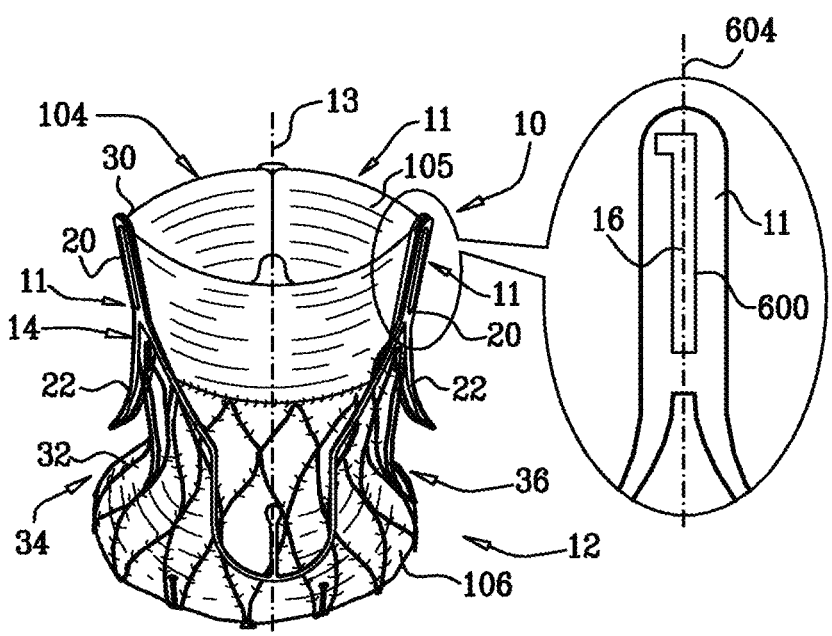

FIGS. 10A and 10B are schematic illustrations of reflection-asymmetric radiographic identifiers 600 on commissural posts 11, in accordance with respective embodiments of the present invention. Identifiers 600 may be used with both the configuration of valve prosthesis 10 described hereinabove with reference to FIG. 1, and that described hereinabove with reference to FIGS. 7C-E. Openings 16 that define radiographic identifiers 600 are shaped to be reflection-asymmetric along respective, post axes 604 that are generally parallel central longitudinal axis 13 of prosthesis 10 when the posts assume their collapsed position. For example, as shown in FIG. 10A, identifiers 600 may be shaped as one or more reflection-asymmetric letters of the alphabet, such as B, C, D, E, etc., or numbers. Alternatively, the identifier may be shaped as any reflection-symmetric symbol, such as the inverted elongated L shown in FIG. 10B. The physician can thus readily identify the true orientation of the selected post that appears to be rotationally aligned with the selected native commissure. If the identifier on the selected post appears in the correct left-right orientation, the selected post is aligned in the desired position (1), as described hereinabove with reference to FIGS. 8A-B. If, on the other hand, the identifier appears as the mirror image of its correct left-right orientation, the selected post is incorrectly rotationally aligned in position (2) as described hereinabove with reference to FIGS. 8A-B. To correct the alignment, the physician rotates the valve prosthesis approximately 60 degrees in either direction, thereby ensuring that one of the two other posts is now rotationally aligned in position (1).

For some applications, such as shown in FIG. 10A, at least one of commissural posts 11 is shaped so as to define both reflection-asymmetric radiographic identifier 600 and another reflection-symmetric shape 610, such as a slit. For example, such a slit may have a mechanical purpose, such as coupling valve 104 to support structures 12 and 14, as described hereinabove with reference to FIG. 1. Alternatively, the physician may use reflection-symmetric shape 610 for rotational orientation as described hereinabove with reference to FIGS. 8A-B in the event that reflection-asymmetric radiographic identifiers 600 are not be clearly visible in the radiographic image during a particular implantation procedure.

For some applications, reflection-asymmetric radiographic identifiers 600 are not defined by openings 16, but instead comprise a material having a radiopacity different from (greater or less than) the radiopacity of other portions of the posts. For some applications, a portion of valve prosthesis 10 other than commissural posts 11 comprises radiographic identifiers 600 (whether defined by openings, or comprising a material having a different radiopacity).

For some applications, techniques described herein are performed in combination with techniques described in a US provisional patent application filed on even date herewith, entitled, "Prosthetic heart valve for transfemoral delivery," which is assigned to the assignee of the present application and is incorporated herein by reference.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 11/024,908, filed Dec. 30, 2004, entitled, "Fluid flow prosthetic device," which issued as U.S. Pat. No. 7,201,772;

International Patent Application PCT/IL2005/001399, filed Dec. 29, 2005, entitled, "Fluid flow prosthetic device," which published as PCT Publication WO 06/070372;

International Patent Application PCT/IL2004/000601, filed Jul. 6, 2004, entitled, "Implantable prosthetic devices particularly for transarterial delivery in the treatment of aortic stenosis, and methods of implanting such devices," which published as PCT Publication WO 05/002466, and U.S. patent application Ser. No. 10/563,384, filed Apr. 20, 2006, in the national stage thereof, which published as US Patent Application Publication 2006/0259134;

U.S. Provisional Application 60/845,728, filed Sep. 19, 2006, entitled, "Fixation member for valve";

U.S. Provisional Application 60/852,435, filed Oct. 16, 2006, entitled, "Transapical delivery system with ventriculo-arterial overflow bypass";

U.S. application Ser. No. 11/728,253, filed Mar. 23, 2007, entitled, "Valve prosthesis fixation techniques using sandwiching";

International Patent Application PCT/IL2007/001237, filed Oct. 16, 2007, entitled, "Transapical delivery system with ventriculo-arterial overflow bypass," which published as POT Publication WO 2008/047354; and/or U.S. application Ser. No. 12/050,628, filed Mar. 18, 2008, entitled, "Valve suturing and implantation procedures."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method comprising the steps of:
providing a valve prosthesis that includes a prosthetic heart valve, wherein the valve prosthesis has a collapsed configuration and an expanded configuration, and at least one radiographic identifier;
wherein the valve prosthesis is configured to have threefold rotational symmetry;
while the valve prosthesis is in the collapsed configuration, placing, via a blood vessel of the subject, the valve prosthesis at least partially in a heart of a subject in a vicinity of a native heart valve having native commissures;
generating a fluoroscopic image of the native commissures and valve prosthesis; and
rotationally aligning the radiographic identifier visible in the image with at least one of the native commissures;
wherein rotationally aligning comprises:
rotating the valve prosthesis;
observing whether the radiographic identifier appears to move in the image in the same direction that the valve prosthesis is rotated, or in an opposite direction; and
if the radiographic identifier appears to move in the image in the opposite direction, rotating the valve prosthesis approximately 60 degrees to correct a rotational alignment of the valve prosthesis.

2. The method of claim 1, wherein the valve prosthesis includes a plurality of commissural posts.

3. The method of claim 2, wherein the valve prosthesis includes exactly three commissural posts.

4. The method of claim 2, wherein the radiographic identifier is shaped to be reflection-asymmetric about a post axis of one of the plurality of commissure posts, which the post axis is generally parallel with a central longitudinal axis of the valve prosthesis when the plurality of commissure posts assume the collapsed configuration.

5. The method of claim 4, wherein the radiographic identifier has a shape of a reflection-asymmetric character.

6. The method of claim 2, wherein the radiographic identifier comprises a material having a first radiopacity that is different from a second radiopacity of the plurality of commissural posts, which material is coupled to each of the plurality of commissural posts.

7. The method of claim 2, wherein the native commissures of the native heart valve include a first native commissure between a left coronary sinus and a right coronary sinus of the native heart valve and wherein rotationally aligning comprises rotationally aligning one of the plurality of commissural posts with the first native commissure.

8. The method of claim 2, wherein at least one of the plurality of commissure posts includes an opening that serves as the at least one radiographic identifier.

9. The method of claim 2, wherein the at least one radiographic identifier is positioned on at least one of the plurality of commissure posts.

10. The method of claim 9, wherein at least one of the plurality of commissure posts includes an opening and the radiographic identifier is positioned adjacent the opening.

11. The method of claim 10, wherein the opening is a reflection-symmetric shape.

12. The method of claim 2, wherein at least one of the plurality of commissural posts is shaped so as to define both reflection asymmetrical radiographic identifier and a reflection-symmetric shape.

13. The method of claim 1, wherein the radiographic identifier is shaped like a letter of the alphabet.

14. The method of claim 1, wherein the radiographic identifier is shaped like a number.

15. The method of claim 1, wherein the radiographic identifier is a slit.

16. The method of claim 1, wherein the radiographic identifier is shaped to be reflection-asymmetric about a longitudinal axis which is generally parallel with a central longitudinal axis of the valve prosthesis when the valve prosthesis assumes the collapsed configuration.

17. The method of claim 1, wherein the radiographic identifier has a shape of a reflection-asymmetric character.

18. The method of claim 1, wherein the valve prosthesis includes a frame, wherein the radiographic identifier comprises a material having a first radiopacity that is different from a second radiopacity of the frame, which material is coupled to the frame.

19. The method of claim 1, wherein the valve prosthesis includes a frame, wherein at least a portion of the frame is shaped so as to define both reflection asymmetrical radiographic identifier and a reflection-symmetric shape.

20. The method of claim 1, wherein the valve prosthesis includes a frame, wherein at least a portion of the frame includes an opening that serves as the at least one radiographic identifier.

* * * * *